United States Patent [19]

Hamas

[11] Patent Number: 4,671,916

[45] Date of Patent: Jun. 9, 1987

[54] METHOD OF INDENTIFYING INSTRUMENTS AS BELONGING TO A SET

[76] Inventor: Robert S. Hamas, Woodhill Medical Park, 8345 Walnut Hill, Suite 120, Dallas, Tex. 75231

[21] Appl. No.: 797,597

[22] Filed: Nov. 13, 1985

[51] Int. Cl.⁴ ............................................. A61B 17/00
[52] U.S. Cl. ................................... 264/249; 29/451; 40/913; 428/67; 428/133; 428/187
[58] Field of Search ...................... 433/75, 77; 40/913; 428/99, 67, 133, 187; 29/451, 525; 264/249

[56] References Cited

U.S. PATENT DOCUMENTS

| | | | |
|---|---|---|---|
| 1,984,839 | 12/1934 | Murray | 40/913 X |
| 2,195,598 | 4/1940 | Olson | 29/525 |
| 3,747,603 | 7/1973 | Adler | 128/341 |
| 3,872,572 | 3/1975 | Hahn | 264/249 X |
| 3,897,534 | 7/1975 | Stephens et al. | 29/525 X |
| 3,935,640 | 2/1976 | Cohan | 433/75 |
| 4,139,664 | 2/1979 | Wenrick | 428/133 X |
| 4,202,351 | 5/1980 | Biche | 128/696 |
| 4,253,830 | 3/1981 | Kazen et al. | 433/77 |

Primary Examiner—Henry F. Epstein
Attorney, Agent, or Firm—Webb, Burden, Robinson & Webb

[57] ABSTRACT

A method of identifying instruments, preferably surgical instruments, as belonging to a set comprises forming at least one bore in a location of each instrument belonging to the set such that said bore will neither substantially weaken the instrument nor interfere with its primary functions. The bore may be cast as part of or drilled partially or completely through each instrument. At least one colored plug of a preferably autoclavable material is then secured in the bore. The colored plug may have a distinctively-shaped head portion, or may have multiple end locks at intermittent positions, the excess of which can be cut away. Most preferably, the method of the invention comprises the step of securing the plug between a pair of differently colored washers. An instrument bearing indicia of a set comprises a colored plug inserted in a bore formed in said instrument and a means for securing said plug in said bore. Most preferably, the plug is made from an autoclavable material selected from either a thermoplastic, a polycarbonate, an elastomer or a metal, such as colorable stainless steel.

13 Claims, 19 Drawing Figures

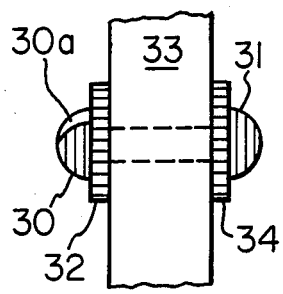
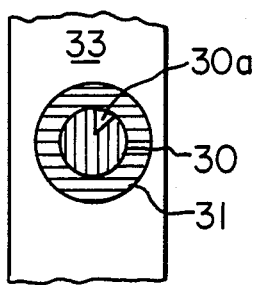
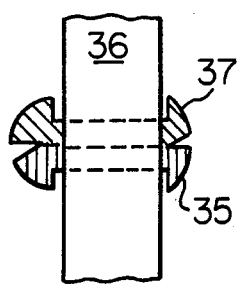
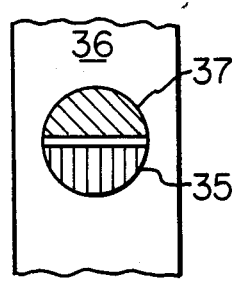
Fig. 4a    Fig. 4b    Fig. 5a    Fig. 5b
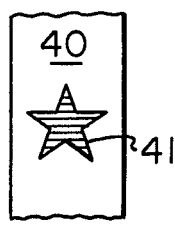
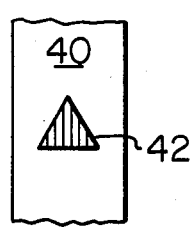
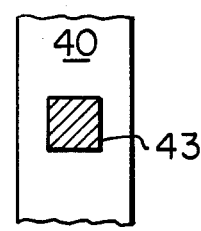
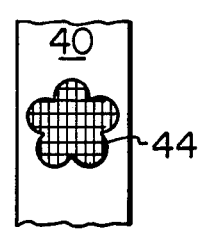
Fig. 6a    Fig. 6b    Fig. 6c    Fig. 6d
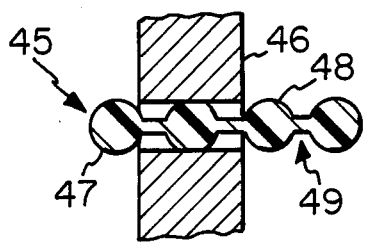
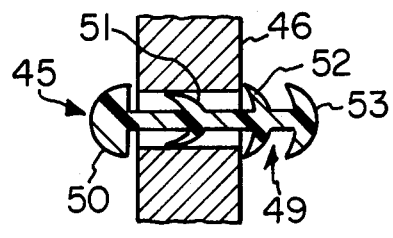
Fig. 7a    Fig. 7b
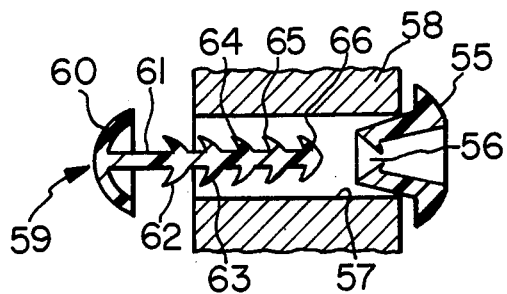
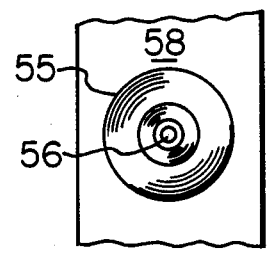
Fig. 8a    Fig. 8b

METHOD OF INDENTIFYING INSTRUMENTS AS BELONGING TO A SET

BACKGROUND OF THE INVENTION

1. Field of the Invention

This invention relates to the field of identifying tools or instruments as belonging to a group or set. In particular, the invention relates to a method of identifying sets of medical or surgical instruments. Further, the invention relates to an instrument bearing indicia of a set to which it belongs.

2. Description of the Prior Art

Surgical instruments are gathered into sets which are kept separately in an operating room. With each instrument assigned to a particular set, it is easier to account for all instruments at any given time.

In the past, operating room personnel have resorted to placing colored, vinyl adhesive tape on the handles of particular instruments to identify them as belonging to a given set. However, surgical instruments are repeatedly sterilized in steam autoclaves. A standard autoclave treatment may exceed 15 minutes where the autoclave is first purged of air with steam and then the contents heated with steam at 121° C. The colored vinyl tape breaks free over time. It is apparently altered by repeated autoclaving. The vinyl tape that remains on the surgical handles gradually chips away due to occasional impacts when instruments are tossed onto a gathering table after use. The vinyl tape identifying also prevents total sterilization of surgical instruments. It may protect bacterial growth therebeneath from sterilization by the autoclaving process. (Interestingly enough, it is not simply the temperature treatment of the autoclaving that destroys the bacteria, but rather the combination of temperature and steam in the absence of air.)

Recently, surgical instrument sets have been introduced with handles that are specially painted to color code the instruments which belong to a given set. The process of painting the handles is understood to be very expensive, to assure that the paint is secured to surgical instruments which are made from stainless steel.

It is not known how durable the painted surgical instruments will be since they have only recently been introduced to the market. However, it is believed that the paint, like the vinyl tape, being in the form of a thin, colored film, is vulnerable to being chipped away over time. Painting is of little use to previously purchased surgical instrument sets. Since the painting process is so special, it is not possible to easily retrofit older instrument sets with painted handles.

It is known in the art that certain utensils can be made from autoclavable elastomers. For example, U.S. Pat. No. 4,253,830 teaches the use of autoclavable plastics in dental bur blocks having color-coded receptacles in which dental drills, grinders and the like can be inserted for cleaning. However, the purpose of these color-coded plastic receptacles is for holding the tools to be autoclaved. The identification means disclosed therein does not permanently attach to the respective instruments belonging to a set.

In U.S. Pat. Nos. 3,747,603, 3,935,640 and 4,202,351, color-coded medical instruments are disclosed but for different purposes. In both U.S. Pat. No. 3,747,603 and No. 4,202,351, the same instrument in each set of instruments is uniformly colored. The color coding does not identify members as belonging to a set but rather is used to identify the size of the synthetic, surgical dilator in U.S. Pat. No. 3,747,603 and the terminal function of lead wires to electrocardiogram monitoring equipment in U.S. Pat. No. 4,202,351. In U.S. Pat. No. 3,935,640, color coding of an area of a dental instrument is taught for determining the depth of insertion of the tip to a periodontal probe. None of the above patents, alone or in combination, teach or suggest the method of identifying instruments and instrument bearing indicia of belonging to a set.

SUMMARY OF THE INVENTION

A method of identifying instruments as belonging to a set according to this invention comprises the step of forming at least one bore in a location on each instrument belonging to the set such that said bore will neither substantially weaken the instrument nor interfere with its primary functions. In existing instrument sets, the bore may be formed by drilling in the location on each instrument. In newly-created sets, the bore may be drilled in or cast as part of each instrument. The bore may be formed partially or completely through a thin, shank portion or the handle portion of an instrument.

The next step comprises securing at least one colored plug in the bore. The plug may have a distinctively-shaped head portion, or may be comprised of a two-pieced, interlocking configuration. Alternatively, the plug to be secured in the bore may have multiple end locks at intermittent positions for use in bores of varying depth. Where plugs of variable length are used, the invention comprises the additional step of cutting off the excess of each plug that protrudes outwardly beyond the bore.

The plug to be inserted into a bore may be self-securing by having a spring-loaded, forked end. Otherwise, the method of the invention includes the steps of inserting a plug in a bore through an instrument, then heading one or both ends of the plug where it emerges from the bore. In a preferred embodiment, the plug is first inserted through a differently colored washer and most preferably through a second washer after insertion through said bore and before securement. In an alternative embodiment, two differently colored half plugs are secured in the bore.

With respect to surgical instruments, no additional steps beyond those mentioned above are required. However, the material selected for manufacture of the plug must be autoclavable. Exemplary of such materials are known thermoplastics, polycarbonates, elastomers and most metals. With respect to the latter group, colorable stainless steels presently used in the manufacture and coating of new surgical instrument handles are preferred. Since the metal plugs would be smaller in size than the entire handle to a surgical instrument, the painting process costs are substantially reduced per set.

The instrument bearing indicia of a set to which it belongs comprises a colored plug of a preferably autoclavable material which is inserted in a bore formed in said instrument and a means for securing said plug in said bore. The plug may have a distinctively-shaped head portion. Alternatively, the plug may be comprised of a first portion inserted into one end of the bore and a second adjustable-length portion inserted into the opposite end of the bore and through the first portion. The securement means comprises a spring-loaded, forked end or multiple end locks attached to said plug.

Because it is desirable that every portion of a surgical instrument be subjected to steam during autoclaving for its complete sterilization, it is preferred that the plug to be secured contain some sort of opening or notch to insure steam penetration even at the point where the plug contacts the metal of the instrument.

The identification method and instrument according to this invention will withstand repeated autoclaving treatments. The invention will allow for the cleaning of all surfaces of each instrument including the plug surfaces. The plugs will not break, wear or chip off. The plugs will not obstruct the instrument user's hand. They will not have any sharp edges which could snag upon and tear surgical gloves or the like.

The invention described herein is most useful in that it may be practiced on newly-created instrument sets or upon existing sets with little effort and expense. The method according to this invention is less costly than painting the stainless steel handles of each instrument. The identifying plug in each instrument is more permanent and more sterile than wrapping each instrument handle with colored, vinyl tape.

BRIEF DESCRIPTION OF THE DRAWINGS

FIG. 4(a) is a side view of a preferred embodiment of the invention using a colored plug in combination with two differently colored washers;

FIG. 4(b) is a front view of FIG. 4(a);

FIG. 5(a) is a side view of an alternative embodiment of two differently colored half plugs secured in a bore;

FIG. 5(b) is a front view of FIG. 5(a);

FIGS. 6(a)–(d) are front views of alternative embodiments of plugs having distinctively-shaped head portions;

FIGS. 7(a)–(b) are cross sections of alternative embodiments of plugs having multiple end locks at intermittent positions;

FIG. 8(a) is a cross section of a two-pieced, interlocking plug in a bore;

FIG. 8(b) is a front view of the right side portion of the plug in FIG. 8(a).

DESCRIPTION OF THE PREFERRED EMBODIMENTS

Figure 1A:
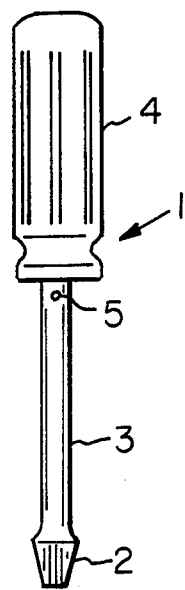
FIG. 1(a) is a view of a mechanical instrument having a bore formed in a location on the instrument.
Figure 1B:
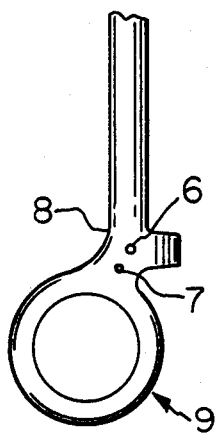
FIG. 1(b) is a view of a portion of a surgical instrument having two bores drilled through the thin, shank portion.
Figure 1C:
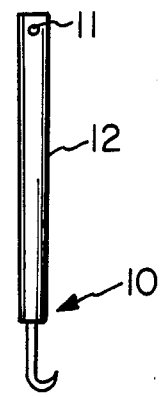
FIG. 1(c) is a view of another surgical instrument having a bore cast as part of the handle portion.

Referring now to FIGS. 1(a) through 1(c), there are shown exemplary mechanical instruments and surgical instruments that belong to respective sets. FIG. 1(a) illustrates a screwdriver 1 comprised of tip 2, shaft 3 and handle portion 4. As it is a primary intent of this invention to form bores in each instrument where the bore will neither substantially weaken the instrument nor interfere with its primary functions, bore 5 is formed in an uppermost portion of shaft 3. Alternatively, bore 5 could have been formed in or through various areas of handle 4.

FIGS. 1(b) and 1(c) show alternative embodiments of the method of the invention. In particular, FIG. 1(b) shows two bores 6, 7 drilled through a thin, shank portion 8 of surgical instrument 9. In FIG. 1(c), surgical instrument 10 is shown having a single bore 11 cast as part of and completely through handle portion 12.

The remaining figures accompanying this application and described herein depict alternative embodiments of plugs in conjunction with bores either partially or completely through locations on an instrument. Although the figures will be described with reference to particular materials or lined for particular colors, it is to be understood that the material that comprises each plug can be made from a variety of known substances and in a variety of colors, shapes and sizes.

Figure 2:
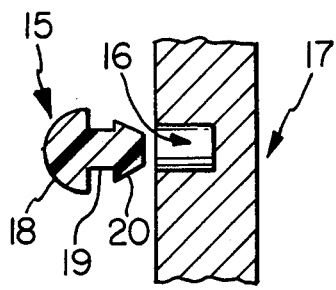
FIG. 2 is a cross section of a plug and a bore formed in a location on an instrument according to the invention.

FIG. 2 shows plug 15 adjacent bore 16 which is formed in but not completely through a location on instrument 17. Plug 15 comprises head portion 18, stem 19 and anchoring portion 20. Anchoring portion 20 has beveled sides for securing plug 15 in bore 16. Alternatively, bore 16 and stem 19 can be correspondingly threaded for securement.

Figure 3A:
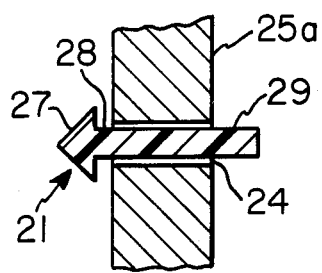
FIG. 3(a) is a cross section of a plug in a bore formed completely through an instrument.

In FIGS. 3(a–c), alternative embodiments of plugs 21, 22 and 23 are shown inserted in bore 24 drilled through instruments 25a, 25b and 25c, respectively. Plugs 21 and 22 which are not self-securing each have a head portion 27 and stem 28. In FIGS. 3(a) and (b), the stem 28 of each plug is first inserted in the bore until head portion 27 contacts with the instrument 25a, 25b. This causes a section 29 of each stem 28 to protrude outwardly beyond the bore 24. The protruding section 29 is then headed to secure the plug where it emerges from bore 24. In FIG. 3(a) plug 21 is made from a thermoplastic material which would have to be heated, melted or deformed to head the protruding section 29 of stem 28 opposite head portion 27.

Figure 3B:
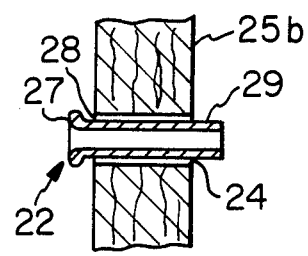
FIG. 3(b) is a cross section of an alternative embodiment of a plug resembling a rivet.

In FIG. 3(b) a metal rivet 22 is shown in cross section. Preferably, when referring to the method of identifying surgical instruments as belonging to a set, the metal rivet 22 of FIG. 3(b) is comprised of a stainless steel that can be electrolytically painted a particular color.

Figure 3C:
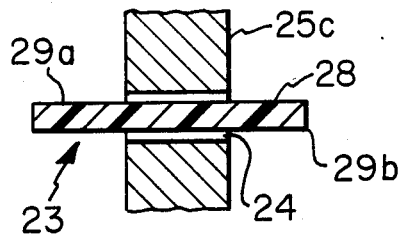
FIG. 3(c) is a cross section of an alternative embodiment of a headless plug in a bore.

In the embodiment shown in FIG. 3(c), the stem 28 of headless plug 23 in bore 24 is shown in cross section through instrument 25c. This type of plug must be headed at both ends 29a and 29b after insertion in bore 24 for securement therethrough by any of the above-mentioned means.

Together, FIGS. 4(a) and 4(b) illustrate a preferred embodiment of the invention. Particularly, dual head portions 30, 31 of a red plug are shown secured through first blue washer 32, instrument 33 and second blue washer 34. Alternatively, the plug can be secured through a differently colored washer on only one side of the bore through an instrument. Note notch 30a in head 30 for providing access by steam to the shank of the plug during autoclave sterilization.

FIGS. 5(a) and 5(b) illustrate an alternative embodiment of the invention which employs two differently colored half plugs for the identification of a greater number of instrument sets. Therein, a yellow half plug 35 is first secured in a bore through instrument 36. Then, green half plug 37 is secured adjacent yellow half plug 35.

Collectively, the four figures that comprise FIG. 6 illustrate a sampling of the various distinctively-shaped heads that respectively colored plugs may have. The plug of FIG. 6(a) has a blue, star-shaped head portion 41 that protrudes outwardly beyond surface 40 of an instrument. FIG. 6(b) shows a red, triangularly-shaped head portion 42. In FIG. 6(c), a green, square-headed plug 43 protrudes beyond surface 40. Lastly, in FI. 6(d), a plug having a yellow petal-shaped head portion 44 is illustrated.

So long as the plug is sized to fit in the bore, any size of bore will suffice. With respect to surgical instruments that are subject to repeated autoclaving, it is found that a bore of between 1/32 or 1/16 and ¼ of an inch in diameter is preferred. A bore of this size should accommodate the thermal expansion of a thermoplastic plug with which it is used.

With respect to certain, thicker tools or instruments, the depth of the bore formed is also of concern. Depending upon the set of instruments to be identified, there may not exist a thin, shank, portion or equally thin handle portion. Since the depth of the bore may vary depending upon its location on an instrument, the invention disclosed herein provides for plugs having multiple end locks at intermittent positions as shown in FIGS. 7(a) and 7(b). Specifically, plug 45 of FIG. 7(a) comprises a plurality of thermoplastic balls attached by a shank to one another and designed for pulling through the bore formed in instrument 46. Plug 45 is pulled through until head portion 47 fits snugly against one end of the bore. Plug 45 is then secured in the bore when ball 48 is positioned outside the bore and opposite head portion 47. Thereafter, the excess of plug 45 can be cut away at 49 and discarded.

FIG. 7(b) shows an alternative embodiment of multiple end lock plug 45 as secured in instrument 46. Note that opposite the head portion 50 of plug 45, a plurality of spring-loaded, forked ends 51, 52 and 53 are located at intermittent positions. When end 53 of plug 45 is inserted into the bore and pulled through, the spring-loaded ends will alternatively engage until head portion 50 is snugly against one end of the bore. This allows for the securement of plug 45 in the bore. Thereafter, the excess of plug 45 that protrudes outwardly beyond the bore can be cut away at 49.

An alternative embodiment of a two-pieced, interlocking plug is illustrated in FIGS. 8(a) and 8(b). The plug comprises a first portion 55 inserted into end 57 of a bore formed in a location on instrument 58. First portion 55 contains an aperture 56 at the center of its innermost end through which a second, adjustable-length portion 59 is threaded. Second portion 59 comprises a head 60, stem 61 and numerous forked ends 62-66. The plug of this embodiment is secured in the bore by pulling the stem 61 of the second portion 59 through first portion 55 until the forked end nearest head 60 engages with aperture 56. The excess of stem 61 can then be cut away.

Plugs for securement in surgical instruments can be manufactured commercially from a variety of autoclavable polycarbonates such as those manufactured by Mobay under the trade names Merlon 8310, 8313 and 8315. The latter types of plastic plugs can assume many different colors and have a UL temperature index of around 120° C. as explained in Modern Plastics Encyclopedia, Volume 57, No. 10(a) (1980–81).

The plugs may also be made from a thermoplastic polyester such as those manufactured by Celanese under the trade name Celanex 3300. This type of plug also comes in a variety of colors and has a UL temperature index of around 130° C. Most preferably, the plugs should be made of a material which can be repeatedly heated to 250° C.

Alternatively, the plugs of the invention can be injection molded of a colorable, butadiene rubber or any other suitable elastomer which is well capable of standing up under repeated autoclaving temperatures.

Having described the presently preferred embodiments of this invention, it is to be understood that it may be otherwise embodied within the scope of the appended claims.

I claim:

1. A method of identifying surgical instruments as belonging to a set comprising the steps of:
    forming at least one bore completely through a thin portion of each surgical instrument belonging to said set such that said bore will not substantially weaken said instrument nor interfere with the primary functions of said instrument; and
    securing at least one colored plug of an autoclavable material selected from the group consisting of a thermoplastic and an elastomer in said bore by inserting said plug in said bore and heading at least one end of said plug where it emerges from said bore.

2. A method of identifying surgical instruments as claimed in claim 1 wherein said bore is cast as part of each instrument.

3. A method of identifying surgical instruments as claimed in claim 3 wherein said bore is drilled completely through said thin portion of each surgical instrument.

4. A method of identifying surgical instruments as claimed in claim 1 wherein said bore is formed in a shank portion of said surgical instrument.

5. A method of identifying surgical instruments as claimed in claim 1 wherein said bore is formed in a handle portion of said surgical instrument.

6. A method of identifying surgical instruments as claimed in claim 1 wherein said method further comprises the step of inserting said colored plug through a differently colored washer made from an autoclavable material before securing said colored plug in said bore.

7. A method of identifying surgical instruments as claimed in claim 6 wherein said method further comprises the step of inserting said colored plug through a second washer after inserting said plug through said bore and before securement.

8. A method of identifying surgical instruments as claimed in claim 7 wherein said plug has a notched head portion.

9. A method of identifying surgical instruments as claimed in claim 1 wherein said colored plug has a distinctively-shaped head portion.

10. A method of identifying surgical instruments as claimed in claim 1 wherein said colored plug has a spring-loaded, forked end.

11. A method of identifying surgical instruments as claimed in claim 1 wherein the size of said bore is about 1/32 to ¼ of an inch in diameter.

12. A method of identifying surgical instruments as claimed in claim 1 wherein said plug has multiple end locks as intermittent positions; and said method further comprises the step of cutting away the excess of said plug protruding outwardly beyond said bore after securement of said plug therethrough.

13. A method of identifying surgical instruments as claimed in claim 1 wherein said plug comprises a first portion inserted into one end of said bore and a second, adjustable-length portion which is inserted into an opposite end of said bore and into said first portion for securement therethrough; and said method further comprises the step of cutting off the excess of said second portion protruding outwardly beyond said first portion.

* * * * *

UNITED STATES PATENT AND TRADEMARK OFFICE
CERTIFICATE OF CORRECTION

PATENT NO. : 4,671,916

DATED : June 9, 1987

INVENTOR(S) : Robert S. Hamas

It is certified that error appears in the above-identified patent and that said Letters Patent is hereby corrected as shown below:

IN THE TITLE: "INDENTIFYING" should read —IDENTIFYING—.

Column 5 Line 6 "FI." shouuld read —FIG.—.

Claim 3 - Column 6 Line 26 "claim 3" should read —claim 1—.

Signed and Sealed this

Fifteenth Day of December, 1987

Attest:

DONALD J. QUIGG

Attesting Officer

Commissioner of Patents and Trademarks